(12) United States Patent
Jadhav et al.

(10) Patent No.: US 8,501,186 B2
(45) Date of Patent: Aug. 6, 2013

(54) ADJUVANT COMPOSITION FOR VACCINE

(75) Inventors: Suresh Sakharam Jadhav, Pune (IN); Bhushan Patwardhan, Pune (IN); Manish Gautam, Pune (IN)

(73) Assignee: Serum Institute of India, Ltd., Pune, Maharashtra (IN)

(*) Notice: Subject to any disclaimer, the term of this patent is extended or adjusted under 35 U.S.C. 154(b) by 431 days.

(21) Appl. No.: 12/774,246

(22) Filed: May 5, 2010

(65) Prior Publication Data
US 2010/0285064 A1 Nov. 11, 2010

(30) Foreign Application Priority Data
May 5, 2009 (IN) ......................... 1184/MUM/2009

(51) Int. Cl.
*A61K 39/00* (2006.01)
*A61K 39/095* (2006.01)
*A61K 31/585* (2006.01)
*A01N 59/02* (2006.01)
*A01N 25/00* (2006.01)

(52) U.S. Cl.
USPC ................. 424/184.1; 424/250.1; 424/714; 514/175; 514/783

(58) Field of Classification Search
None
See application file for complete search history.

(56) References Cited

U.S. PATENT DOCUMENTS

| | | | |
|---|---|---|---|
| 7,108,870 B2* | 9/2006 | Sangwan et al. | 424/725 |
| 2004/0033273 A1* | 2/2004 | Patwardhan et al. | 424/725 |
| 2010/0285064 A1* | 11/2010 | Jadhav et al. | 424/227.1 |

OTHER PUBLICATIONS

Weintraub (Carbohydrate Research. 2003; 338: 2539-2547).*
Fahnert ("Using Folding Promoting Agents in Recombinant Protein Production: A Review" in Recombinant Gene Expression: Reviews and Protocols, Third Edition of Methods in Molecular Biology. 2012; 824: 2-36).*
Gautam et al. (International Immunopharmacology. 2004; 4: 841-849).*
Amara et al. (Phharamceutical Biology. 1999; 37 (4): 253-259).*
Bhushan et al. Derwent publication abstract No. IN 200301253; Jan. 20, 2006.*

* cited by examiner

Primary Examiner — Shanon A Foley
(74) Attorney, Agent, or Firm — Robert P. Michal; Lucas & Mercanti, LLP

(57) ABSTRACT

The present invention provides a *Withania somnifera* fraction rich in withanolides and a vaccine comprising a "*Withania somnifera* fraction" as an adjuvant.

9 Claims, 12 Drawing Sheets

ADJUVANT COMPOSITION FOR VACCINE

CROSS-REFERENCE TO RELATED APPLICATIONS

This application claims priority to and benefit of Indian Application No. 1184/MUM/2009 filed on May 5, 2009, the content of which is incorporated herein by reference in its entirety.

FIELD OF THE INVENTION

The present invention relates to a plant fraction obtained from the roots of plant *Withania somnifera*.

The present invention envisages a vaccine comprising novel adjuvant capable of invoking T cell dependent immune responses to T cell independent antigens such as polysaccharide.

BACKGROUND OF THE INVENTION

*Withania somnifera* is commonly known as Ashwagandha, Indian ginseng, Winter cherry and Ajagandha. It is mainly used in herbal formulations of the Ayurvedic or Indian system of medicine for treating memory loss, tumors, inflammation, arthritis, asthma and hypertension. The main constituents of ashwagandha are alkaloids and steroidal lactones. Among the various alkaloids, withanine is the main constituent. The other alkaloids are somniferine, somnine, somniferinine, withananine, pseudo-withanine, tropine, pseudo-tropine, 3-a-gloyloxytropane, choline, cuscohygrine, isopelletierine, anaferine and anahydrine. Two acyl steryl glucoside viz. sitoindoside VII and sitoindoside VIII have been isolated from root. The leaves contain steroidal lactones, which are commonly called withanolides. The withanolides have C28 steroidal nucleus with C9 side chain, having six membered lactone ring. Apart from leaves withanolides are also present in roots and berries.

Following patents/applications disclose processes for the preparation of *Withania somnifera* extract.

U.S. Pat. No. 6,713,092 discloses a process of making an *Withania somnifera* extract composition which comprises (a) providing root stock and leaves of a *Withania somnifera* plant which is about 1-2 years old, (b) extracting said root stock and leaves with an aqueous-alcoholic solvent in the presence of a exogenous saccharide, c) concentrating the extract under vacuum, (d) treating the residue with an apolar organic solvent to remove free withanolide A aglycones therefrom, (e) vacuum the insoluble residue of such treatment below about 60.degree. C. to provide a dry solid, and (f) pulverizing the solid under controlled temperature and humidity conditions, to obtain the desired powder product.

U.S. Pat. No. 6,153,198 discloses a process of making the extract of *Withania somnifera* which comprises (a) providing root stock of a *Withania somnifera* plant which is about 1-2 years old, (b) extracting said root stock with an aqueous-alcoholic solvent, (c) concentrating the extract under vacuum, (d) treating the residue with an apolar organic solvent to remove free withanolide A aglycones therefrom, (e) vacuum drying the insoluble residue of such treatment below about 60° C. to provide a dry solid, and (f) pulverizing the solid under controlled temperature and humidity conditions, to obtain the powder product. The aqueous-alcoholic solvent used is water-methanol or water-ethanol and the organic solvent used is chloroform or ethyl acetate.

US 20040033273 discloses a method for obtaining a composition having immune stimulating activity or anti-tumor activity from *Withania somnifera* comprising: (a) contacting *Withania somnifera* plant or plant part with a first medium polar solvent to produce a particulate suspension; (b) clarifying the particulate suspension to produce a clarified first solution and a first residue; (c) evaporating the solvent from the first clarified solution to produce a fraction, denoted fraction A; (d) resuspending the first residue in a second polar solvent thereby producing a second solution and a second residue; (e) clarifying the second solution to produce a second clarified solution; (f) evaporating the second polar solvent from the second clarified solution to produce a fraction, denoted fraction B; (g) resuspending the second residue in a third solvent more polar than the second polar solvent thereby producing a third solution and a third residue; (h) clarifying the third solution to produce a third clarified solution; (i) evaporating the third solvent from the third clarified solution to produce a fraction, denoted fraction C; (j) combining fractions A, B and C to produce an extract; (k) resuspending the extract in a solution to produce a fourth alkaline solution; and (l) fractionating the fourth solution with a non polar solvent and removing the solvent to produce a composition having immune stimulating activity or anti-tumor activity. The first residue is resuspended in a solvent having about 50% ethanol or about 40 to 60% isopropyl alcohol. The first medium polar solvent comprises acetone, tetrahydrofuran or ethylacetate. The second solvent comprises a mixture of water and isopropyl alcohol (IPA).

U.S. Pat. No. 7,108,870 discloses a process for isolation of withaferin-A from plant materials, said process comprising the steps of: (i) extracting the plant materials in an aqueous alcohol extraction solvent, (ii) defatting the extract, as obtained in step (i), with partitioning with n-hexane followed by chromatographic separation to obtain a withanolide preparation, (iii) portioning out withanolide aglycones from the withanolide preparation, as obtained in step (ii), into chloroform followed by evaporation of said chloroform to obtain a chloroform extract, and (iv) dissolving the chloroform extract as obtained in step (iii) in methanol followed by chromatographic separation to obtain withaferin-A.

The extraction is performed using a 60:40 methanol:water extraction solvent.

The prior art discusses crude *Withania somnifera* extract preparation methods which are not sufficient to produce a biologically active product. Accordingly, it is desirable to develop a process for the preparation of *Withania somnifera* fraction which is rich in withanolides.

Vaccines based on polysaccharide antigens are well known. The capsular polysaccharides of *Neisseria meningitidis* are attractive vaccine candidates because they constitute the most highly conserved and most exposed bacterial-surface antigens. The use of capsular polysaccharides as immunoprophylactic agents against human disease caused by encapsulated bacteria is now firmly established. The capsular polysaccharides of the meningococcus are negatively charged and are obtained in a high molecular weight immunogenic form by precipitation. Meningococcal polysaccharide vaccines are efficacious to protect from meningitis disease in adults, but cannot provide full protection to infants under the age of 5.

The duration of protection elicited by the meningococcal polysaccharide vaccines is not long lasting in adults and children above four years of age. For children from one to four years old the duration of protection is less than three years. Protective immunity to encapsulated bacterial pathogens such as *N. meningitidis* is principally mediated by the reaction between antibody and capsular polysaccharide epitopes. In encapsulated gram negative bacteria, protection results primarily from a direct complement-mediated bactericidal effect.

Vaccines have been prepared from the capsular polysaccharides of *Neisseria meningitidis* (groups A, C, W-135 and Y). These and other polysaccharides have been classified as T cell independent type 2 (TI-2) antigens based on their inability to stimulate an immune response in animals that carry an X-linked immune B-cell defect. TI-2 antigens tend to be characterized by high molecular weight, multiple repeat epitopes, slow degradation in vivo and a failure to stimulate major histocompatibility complex (MHC) type II mediated T-cell help. TI-2 antigens generally are incapable of stimulating an immune response in neonatal humans under 18 months of age.

Polysaccharide antigens are T-lymphocyte independent antigens and therefore, IgG response elicited by the antigens is very limited. Moreover, the immune response elicited by polysaccharide antigens is characterized by low immunological memory and therefore the immunity induced by the use of such antigens is short lived. Further, young children respond poorly to polysaccharide antigens and therefore vaccines containing them have not been proven to be effective in young children. To enhance the immune response elicited by polysaccharide antigens, aluminium salts have been known to be used as adjuvants in vaccines containing these antigens. However, aluminium containing vaccines, when injected, have been reported to cause undesirable local reactions.

U.S. Pat. No. 6,645,495 discloses a composition comprising an antigen or a nucleic acid encoding an antigenic peptide or protein, a saponin adjuvant such as Quil-A, QS-7 and QS-21, and an excipient selected from a group consisting of beta cyclodextrin and human serum albumin.

However, Quillaja saponins have been found to be unstable in aqueous phase (Sun, Hong Xiang et al., 2009, Vaccine, vol. 27, p. 1787-1796). Quillaja saponins have strong haemolytic effect and also cause undesirable local reactions like swelling, skin degeneration. Even the deaths of mice used in the experiments have been reported due to presence of Quillaja saponins (Ronnberget et at., vaccine, vol. 13, 1995, 1375-1382.)

The Indian patent application No. 1253/MUM/2003 published on 20 Jan. 2006 discloses the use of *Withania somnifera* extract as an adjuvant in vaccines. However, it does not provide adjuvant composition for vaccines based on polysaccharide antigens such as meningococcal vaccine prepared from polysaccharides of *Neisseria meningitides*. Further, the disclosed crude extract is known to contain a large proportion of polysaccharides that could adversely affect the bioavailability of the active compounds present therein. Moreover, to attain the desired adjuvanticity, large quantity of the extract is required to be used in the vaccine.

Accordingly, it is desirable to develop highly pure adjuvant which has greater immune adjuvant activity than crude *Withania somnifera* extract. Further, there is also need of a vaccine comprising this adjuvant and vaccine antigen which provides enhanced immunological response in the host.

OBJECTS OF THE INVENTION

It is an object of the present invention is to provide a novel process for the preparation of *Withania somnifera* fraction rich in withanolides.

It is another object of the present invention to provide a process for preparing an enriched plant fraction containing a mixture of Withaferin A and Withanolide A, obtained from the roots of plant *Withania somnifera*.

It is still another object of the present invention to provide a *Withania somnifera* fraction which contains a specific ratio of Withanolide A to Withaferin A in combination with other components.

It is yet another object of the present invention to provide a simple process for the preparation of *Withania somnifera* fraction.

It is a further object of the present invention to provide a process for the preparation of *Withania somnifera* fraction which is high yielding.

It is still further object of the present invention to provide a process for the preparation of *Withania somnifera* fraction which is economic.

It is another object of the present invention to provide a vaccine adjuvant for polysaccharide antigens which has enhanced immune adjuvant activity than crude *Withania somnifera* extract.

It is still another object of the present invention to provide a vaccine containing adjuvant which comprises advantageous percentage of withanolides which are capable of engaging T cell help to T cell independent antigens.

SUMMARY OF THE INVENTION

In accordance with the present invention there is provided a process for preparing a *Withania somnifera* fraction rich in withanolides; said process comprising the following steps:
  a) obtaining coarse root material from the *Withania somnifera* plant and refluxing with hot water to obtain a slurry;
  b) filtering and vacuum concentrating the slurry to obtain a concentrated aqueous extract;
  c) liquid-liquid successive partitioning of the concentrated aqueous extract with at least one non-polar organic solvent & at least one polar organic solvent to obtain an organic fraction of the extract; and
  d) concentrating and co-distilling the organic fraction under vacuum to remove the traces of solvent followed by drying the fraction at a temperature not more than 70° C. to obtain a *Withania somnifera* fraction rich in withanolides.

Typically, the non polar organic solvent is selected from the group consisting of n-hexane, toluene and benzene.

Typically, the polar organic solvent is selected from the group consisting of butanol, dichloromethane, dichloroethane and chloroform.

In accordance with another aspect of the present invention there is also provided a *Withania somnifera* fraction rich in withanolide.

In accordance with the present invention the *Withania somnifera* fraction comprises a) withanolide A of about 0.5-1%; b) withaferin A of about 0.1-0.6%; c) withanolide B of about 0.01-0.1%; d) withanoside IV of about 0.8-1.2%; e) withanoside V of about 0.5-0.8%; and f) 12-deoxy withastramonolide of about 0.8-1.2%.

Typically, the ratio of withaferin A and withanolide A is in the range of about 1:2 to 1:5.

In accordance with another aspect of the present invention there is provided a vaccine; said vaccine comprising:
  A. at least one vaccine antigen
  B. a "*Withania somnifera* fraction" as an adjuvant, said *Withania somnifera* fraction, comprising at least one ingredient selected from the group consisting of withanolide A, withaferin A, withanolide B, withanoside IV, withanoside V, and 12-deoxy withastramonolide, said fraction being present in an amount of about 85 to 99% of the mass of the antigen.

Typically, the proportion of Withanolide A is in the range of about 0.1 to about 5% of the mass of the fraction.

Typically, the proportion of Withaferin A is in the range of about 0.1 to about 3% of the mass of the fraction.

Typically, the proportion of Withanolide B is in the range of about 0.03 to about 1.4% of the mass of the fraction.

Typically, the proportion of Withanoside IV is in the range of about 0.40 to about 3% of the mass of the fraction.

Typically, the proportion of Withanoside V is in the range of about 0.25 to about 3% of the mass of the fraction.

Typically, the proportion of 12-deoxy withastramonolide is in the range of about 0.1 to about 3% of the mass of the fraction.

In accordance with the preferred embodiment of the present invention, the *Withania somnifera* fraction comprises a) withanolide A in an amount of about 0.1 to 5% of the mass of the fraction and b) withaferin A in an amount of about 0.1 to 3% of the mass of the fraction.

Typically, the vaccine antigen is bacterial polysaccharides selected from the group consisting of polysaccharides obtained from *Neisseria meningitidis, Escherichia coli, Francisella tularensis, Haemophilus influenzae, Klebsiella, Moraxella catarrhalis Klebsiella, Porphyromonas gingivalis, Pseudomonas aeruginosa, Burkholderia cepacia, Salmonella typhi, Salmonella typhimurium, Salmonella paratyphi, Shigella dysenteriae, Shigella flexneri, Shegella sonnei, Vibrio cholera, Enterococcus faecalis, Enterococcus faecium*, Group A *Streptococcus*, Group B *Streptococcus, Mycobacterium tuberculosis, Staphylococcus aureus, Staphylococcus epidermidis* and *Streptococcus pneumoniae*.

Typically, the vaccine antigen is meningococcal polysaccharide selected from serogroups A, C, Y and W-135 of *Neisseria meningitidis*.

Typically, the vaccine antigen is a protein selected from the group consisting of proteins obtained from *Corynebacterium diphtheriae, Bordetella pertussis, Clostridium tetani* and hepatitis B virus.

In accordance with another embodiment of the present invention the vaccine further comprises at least one co-adjuvant selected from the group consisting of alum-hydroxide, plant alkaloid, detergent, QS-21, CpG, MPL, MF-59, AS02, AS04, cytokines, a block copolymer or biodegradable polymer.

Typically, the plant alkaloid is tomatine.

Typically, the detergent is selected from the group consisting of saponin, polysorbate 80, Span 85 and Stearyl tyrosine.

In accordance with still another embodiment of the present invention the vaccine further comprises at least one TLR agonist; at least one imidazo-quinoline immune response modifier; and at least one double stem loop immune modifier (dSLIM).

Typically, the TLR agonist is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen.

Typically, the imidazoquinoline immune response modifier is selected from the group consisting of resiquimod (R848), imiquimod and gardiquimod.

BRIEF DESCRIPTION OF THE DRAWINGS

The invention will now be described with reference to the accompanying drawing in which.

DETAILED DESCRIPTION OF THE INVENTION

Figure 1:
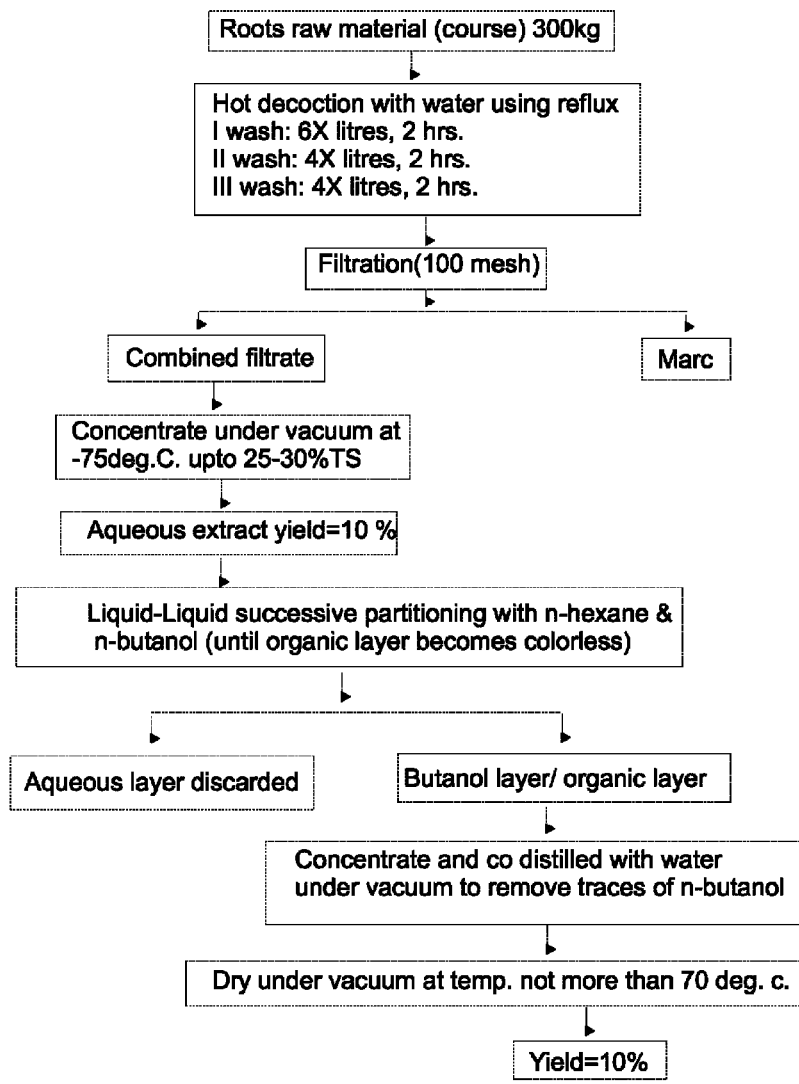
FIG. 1 illustrates a process for the preparation of a *Withania Somnifera* fraction rich in withanolide in accordance with the present invention.

The process of the present invention is directed to obtain a *Withania somnifera* fraction rich in withanolides from a crude aqueous *Withania somnifera* root extract.

In accordance with the present invention there is provided a process for preparing a *Withania somnifera* fraction rich in withanolides; said process comprising the following steps:

First step is obtaining coarse root material from the *Withania somnifera* plant and refluxing with hot water to obtain a slurry. The obtained slurry is then filtered and vacuum concentrated to obtain a concentrated aqueous extract.

The next step is liquid-liquid successive partitioning of the concentrated aqueous extract with at least one non-polar organic solvent and at least one polar organic solvent to obtain an organic fraction of the extract. The obtained the organic fraction is then concentrated and co-distilled under vacuum to remove the traces of organic solvent followed by drying the fraction at a temperature not more than 70° C. to obtain a *Withania somnifera* fraction rich in withanolides.

Typically, the non polar organic solvent is selected from the group consisting of n-hexane, toluene and benzene.

Typically, the polar organic solvent is selected from the group consisting of butanol, dichloromethane, dichloroethane and chloroform.

In accordance with another aspect of the present invention there is also provided a *Withania somnifera* fraction rich in withanolides.

In accordance with the present invention the *Withania somnifera* fraction comprises a) withanolide A of about 0.5-1%; b) withaferin A of about 0.1-0.6%; c) withanolide B of about 0.01-0.1%; d) withanoside IV of about 0.8-1.2%; e) withanoside V of about 0.5-0.8%; and f) 12-deoxy withastramonolide of about 0.8-1.2%.

Typically, the ratio of withaferin A and withanolide A is in the range of about 1:2 to 1:5.

In particular the *Withania somnifera* fraction obtained by the present process is rich in 20 to 40 times more withanolides as compared to the crude extracts of prior art disclosures.

In accordance with another aspect of the present invention there is provided a vaccine; said vaccine comprising:
A. at least one vaccine antigen
B. a "*Withania Somnifera* fraction" as an adjuvant, said *Withania somnifera* fraction, comprising at least one ingredient selected from the group consisting of withanolide A, withaferin A, withanolide B, withanoside IV, withanoside V, and 12-deoxy withastramonolide, said fraction being present in an amount of about 85 to 99% of the mass of the antigen.

Typically, the proportion of withanolide A is in the range of about 0.1 to about 5% of the mass of the fraction.

Typically, the proportion of withaferin A is in the range of about 0.1 to about 3% of the mass of the fraction.

Typically, the proportion of withanolide B is in the range of about 0.03 to about 1.4% of the mass of the fraction.

Typically, the proportion of withanoside IV is in the range of about 0.40 to about 3% of the mass of the fraction.

Typically, the proportion of withanoside V is in the range of about 0.25 to about 3% of the mass of the fraction.

Typically, the proportion of 12-deoxy withastramonolide is in the range of about 0.1 to about 3% of the mass of the fraction.

In accordance with the preferred embodiment of the present invention, the *Withania Somnifera* fraction comprises a) Withanolide A in an amount of about 0.1 to 5% of the mass of the fraction and b) Withaferin A in an amount of about 0.1 to 3% of the mass of the fraction.

Typically, the ratio of withaferin A and withanolide A is in the range of about 1:2 to 1:5.

Typically, the vaccine antigen is bacterial polysaccharides selected from the group consisting of polysaccharides obtained from *Neisseria meningitidis*, *Escherichia coli*, *Francisella tularensis*, *Haemophilus influenzae*, *Klebsiella*, *Moraxella catarrhalis*, *Porphyromonas gingivalis*, *Pseudomonas aeruginosa*, *Burkholderia cepacia*, *Salmonella typhi*, *Salmonella typhimurium*, *Salmonella paratyphi*, *Shigella dysenteriae*, *Shigella flexneri*, *Shegella sonnei*, *Vibrio cholera*, *Enterococcus faecalis*, *Enterococcus faecium*, Group A *Streptococcus*, Group B *Streptococcus*, *Mycobacterium tuberculosis*, *Staphylococcus aureus*, *Staphylococcus epidermidis* and *Streptococcus pneumoniae*.

Typically, the vaccine antigen is meningococcal polysaccharide selected from serogroups A, C, Y and W-135 of *Neisseria meningitidis*.

Typically, the vaccine antigen is a protein selected from the group consisting of proteins obtained from *Corynebacterium diphtheriae*, *Bordetella pertussis*, *Clostridium tetani* and hepatitis B virus.

In accordance with another embodiment of the present invention the vaccine further comprises at least one co-adjuvant selected from the group consisting of alum-hydroxide, plant alkaloid, detergent, QS-21, CpG, MPL, MF-59, AS02, AS04, cytokines, a block copolymer or biodegradable polymer.

Typically, the plant alkaloid is tomatine.

Typically, the detergent is selected from the group consisting of saponin, polysorbate 80, Span 85 and Stearyl tyrosine.

In accordance with still another embodiment of the present invention the vaccine further comprises at least one TLR agonist; at least one imidazo-quinoline immune response modifier; and at least one double stem loop immune modifier (dSLIM).

Typically, the TLR agonist is selected from the group consisting of lipopolysaccharide, peptidoglycan, polyl:C, CpG, 3M003, flagellin, *Leishmania* homolog of eukaryotic ribosomal elongation and initiation factor 4a (LeIF) and at least one hepatitis C antigen.

Typically, the imidazoquinoline immune response modifier is selected from the group consisting of resiquimod (R848), imiquimod and gardiquimod.

Following examples illustrate the invention, but are not intended to limit the scope of the present invention.

EXAMPLES

Example 1

Chemical Characterization of *Withania somnifera* Fraction of the Present Invention (SIIL-F-4)

LC-MS fingerprint of *Withania somnifera* fraction was developed towards identification of constituents.

a) Sample Preparation for LC-MS Analysis:

Sample was prepared by sonication-extraction of weighed amount of extract (0.4 gm) with 10 ml of methanol at a room temperature for 10 minutes. Marker compounds (1 mg/ml) in methanol were also sonicated for 10 minutes at room temperature for maximum dissolution. The resulting *Withania somnifera* extract (WSE) suspension was filtered through a 0.22μ, membrane filter (Pall Corporation, Mumbai, India) prior to analysis. The volume of injection was optimized at 10 μl.

b) Identification and Quantification of Marker Compounds in the *Withania somnifera* Fraction of the Present Invention Marker compounds were identified and quantified in the *Withania somnifera* fraction by using HPLC. (Table 1)

TABLE 1

| | | | |
|---|---|---|---|
| Column | RP C-18 Luna phenomenex (250 × 4.6 mm) | | |
| Column oven temperature | 25° C. | | |
| Mobile phase | 1.36 g of anhydrous Potassium dihydrogen orthophosphate (KH$_2$PO$_4$) was dissolved in 900 ml of HPLC grade water (obtained from Millipore, Milli-Q Water purification system) and the p$^H$ was adjusted to 2.58 using 10.0% orthophosphoric acid solution. The volume was adjusted to 1000 ml with water and was then filtered through 0.45 μ membrane and degassed in a sonicator for 3 minutes. B-Acetonitrile | | |
| Flow rate | 1.5 ml | | |
| Injection volume | 25.0 μl | | |
| Gradient | Time | A conc | B. Con |
| | 0.01 | 95 | 5 |
| | 18.00 | 55 | 45 |
| | 25.00 | 20 | 80 |
| | 28.00 | 20 | 80 |
| | 35.00 | 45 | 45 |
| | 40.00 | 95 | 5 |
| | 45.00 | 95 | 5 |
| | 45.00 | Stop | |
| Detector | SPD- M 10 Avp Photo diode array detector | | |
| Wave length | 227 nm | | |
| Standard preparation | Withanoside-IV - 5.83 mg: Withanoside V - 4.9 mg; Withaferin A - 2.72 mg; 12 deoxy withastramonolide - 2.82 mg; Withanolide-A 2.45 mg & Withanolide-B - 2.35 mg were dissolved in 25 ml methanol & then volume was adjusted to 50 ml. | | |

TABLE 1-continued

| | |
|---|---|
| Sample preparation | ~20002.8 mg of extract was transferred to a 100 ml volumetric flask and dissolved in methanol followed by sonication for 10 to 15 minutes. Further the sample was boiled using water bath for 15 to 20 minutes and cooled. Then the volume was adjusted to 100 ml with methanol and filtered through 0.45 µ membrane filter paper. |

Separations were carried out using reversed column BDS Hypersil C-18 column (particle size, 5 µm; dimensions, 250× 4.6 mm, Thermo electron corporation) maintained at 50° C. The mobile phase consisted of water (A) and mixture of methanol and reagent alcohol (B) in the ratio of 1:1. Reagent alcohol is denatured ethanol and consists of ethanol, methanol and 2-propanol in the ratio of 90.6:4.5:4.9.

Analysis was done using gradient elution as 65A/35B to 55A/45B during run time of 25 min. Flow rate was kept at 1 ml/min and each run was followed by wash with 100% of acetonitrile (B) for 5 min and equilibration period of 10 min.

The results are shown in table 2.

TABLE 2

| Analysis | Specification | Results |
|---|---|---|
| Identity | HPLC-PDA detection | |
| Total withanolide by HPLC (As calculated on the basis of w/w content of Withanolide A, withaferin A, Withanolide B, withanoside IV, Withanoside V and 12-deoxy withastramonolide) | NLT 2% | 4% |

| Content of withanolides | % (w/w) |
|---|---|
| Withanolide A | 0.74 |
| Withaferin A | 0.17 |
| Withanolide B | 0.07 |
| withanoside IV | 1.06 |
| Withanoside V | 0.54 |
| 12-deoxy withastramonolide | 0.86 | c) LC-MS/MS Details

LC-MS analysis was performed in the positive atmospheric pressure electrospray ionisation (ESI) API-2000 (Applied Biosciences/MDS SCIEX, USA) equipped with triple quadrupole detection mode. (The optimized MS conditions: ionization source voltage 5500 V and source temperature 450° C.). Scanning range was kept from m/z 50-1200 (amu). The data acquisition was done using Analyst 1.4.2 software (MDS SCIEX).

LC-MS fingerprint shows the presence of 10 peaks (Table 3)

TABLE 3

| Peak no | $t_R$ | MS/MS data (m/z) | Identification if any |
|---|---|---|---|
| 1 | 4.60 | 940; 919; 897; 834; 715.3; 475.4; 453.3; 307.2; 180.1 | Not available in literature |
| 2 | 5.52 | 832.3; 778.4; 721.5; 549; 473.3; 344; 252.2; 177.3 | Not available in literature |
| 3 | 8.09 | 816.3; 675.2; 670.4; 473.2; 437; 187.2 | Not available in literature |
| 4 | 9.97 | 950.5; 592.3; 549.3; 511.3; 506.2; 489.3; 439.3; 185.4 | Not available in literature |
| 5 | 12.98 | 872.5; 821.4; 816.4; 799.2; 637.2; 457.3; 439.2; 258.1; 149.3 | Not available in literature |
| 6 | 13.73 | 856.4; 800.4; 783.4; 621.3; 473.3; | Not available in |

TABLE 3-continued

| Peak no | $t_R$ | MS/MS data (m/z) | Identification if any |
|---|---|---|---|
| | | 459.3; 441.3; 391.3; 247.1; 130.3 | literature |
| 7 | 14.55 | 963.4; 941.5; 493.2; 488.2; 471.3; 341.4; 299.1; 281.0 | Marker I (external standard) |
| 8 | 16.03 | 488.3; 471.1; 459.2; 435.4; 399.3; 315.2; 299.4; 263.1 | Marker III (literature report) |
| 9 | 17.75 | 958.3; 488.4; 471.3; 453.2; 417.3; 289.3; 262.9 | Marker II (external standard) |
| 10 | 19.71 | 954.1; 791.3; 659.4; 643.5; 459.1; 441.2; 351.2; 155.1 | Not available in literature |

Figure 2:
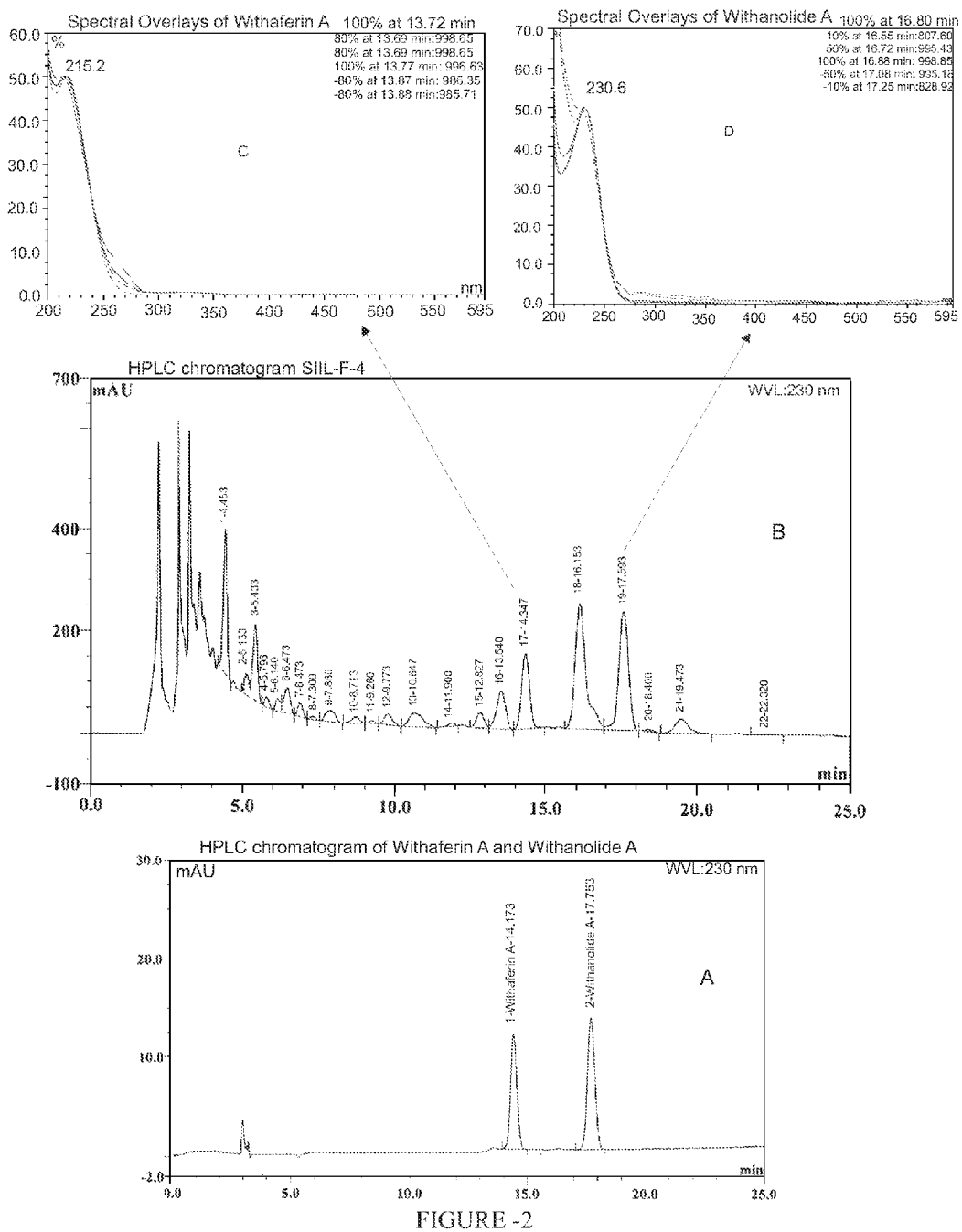
FIG. 2 illustrates identification of marker compounds on the basis of retention time and UV spectral matching with standard markers.
Figure 3:
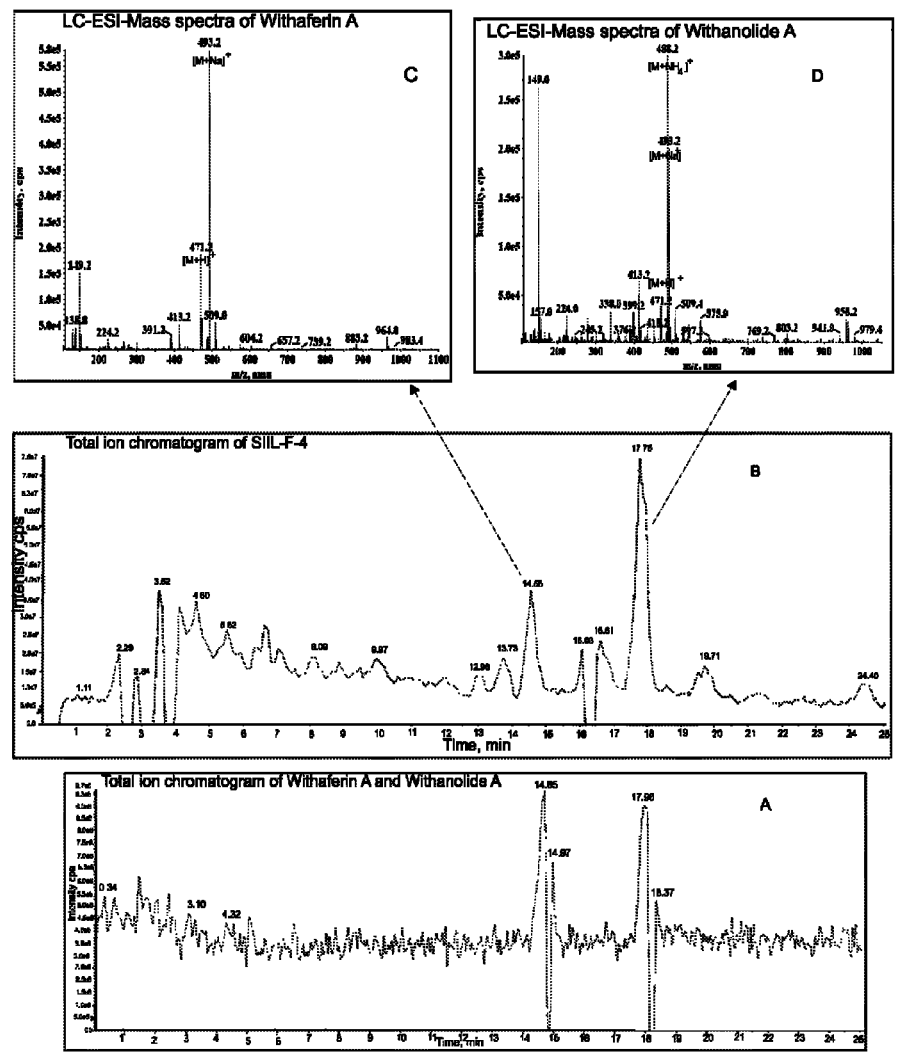
FIG. 3 illustrates identification of marker compounds on the basis of LC-MS analysis.

$t_R$: retention time d) LC-MS Profile of *Withania somnifera* Fraction of the Present Invention (SIIL-F-4)

i) Marker compounds were identified on the basis of retention time and UV spectral matching with standard markers as shown in FIG. 2 wherein, A=HPLC chromatogram of standard marker compounds; B=HPLC chromatogram of *Withania somnifera* fraction of the present invention (SIIL-F-4); C=Spectral overlays of compound 1; D=Spectral overlays of compound II.

ii) Marker compounds were confirmed on the basis of LC-MS analysis as shown in FIG. 3 wherein, A=Total ion chromatogram of standard compound; B=Total ion chromatogram of SIIL-F-4; C=Mass spectra of compound IA and D=Mass spectra of compound II e) Content Analysis:

Detection of Withaferin A and withanolide A contents in various fractions obtained from successive fractionation of *Withania somnifera* extract.

The fractions, marker, extract were analyzed for Withaferin A & Withanolide A using HPLC-DAD analysis and are reported here as mg/100 mg of test material.

Figure 4:
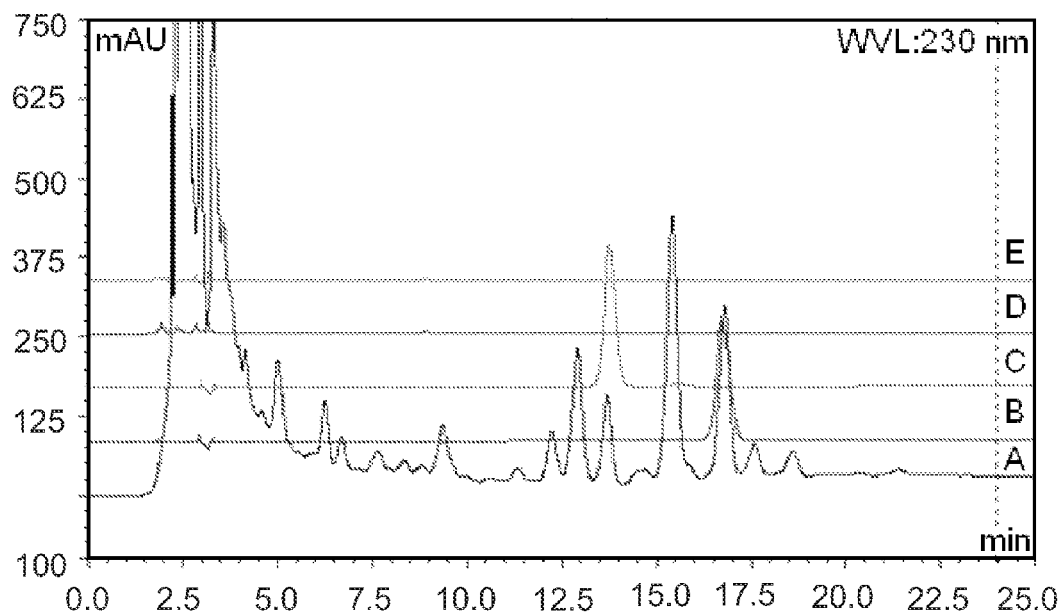
FIG. 4 illustrates HPLC-DAD chromatograms of various fractions obtained from successive fractionations of *Withania Somnifera* extract (WSE) and reference standards.

HPLC-DAD chromatograms of various fractions obtained from successive fractionations of WSE and reference standards are shown in FIG. 4, wherein A=HPLC chromatograms of n-butanolic fraction; reference standards such as withanolide A (B) and withaferin A(C); D=methanolic fraction; and E=aqueous fraction f) Marker Content Analysis of Withaferin A and Withanolide A in Various Fractions of *Withania somnifera* (WS) Extract is Provided in Table 4.

TABLE 4

| Sr. no. | Name of fraction | Withaferin A (mg/100 mg ± SD) | Withanolide A (mg/100 mg ± SD) |
|---|---|---|---|
| 1 | WS- n-butanol (Present invention) | 0.853 ± 0.005 | 1.75 ± 0.009 |
| 2 | WS Methanol P | ND | ND |
| 3 | WS aqueous P | ND | ND |
| 4 | WSE (patent application 1253/MUM/2003) | 0.021325 ± 0.005 | 0.04375 ± 0.009 |

*ND = Not detectable g) Marker Content

Marker content in *Withania somnifera* fraction of the present invention was calculated by HPLC and is shown in table 5.

TABLE 5

| Batch | Withaferin A (mg/100 mg) | Withanolide A (mg/100 mg) |
|---|---|---|
| FRACTION (Lab scale) | 0.385 ± 0.003 | 0.742 ± 0.007 |
| FRACTION (Scaled up) | 0.853 ± 0.005 | 1.750 ± 0.009 |

Example 2

Figure 5:
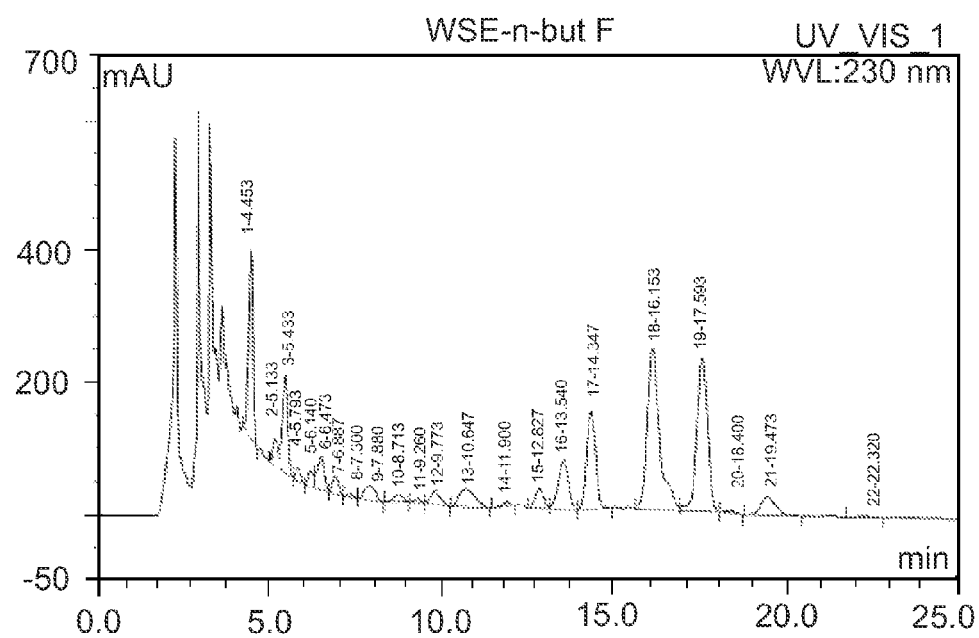
FIG. 5 illustrates chemo-profiling of *Withania Somnifera* fraction in accordance with the present invention.
Figure 6:
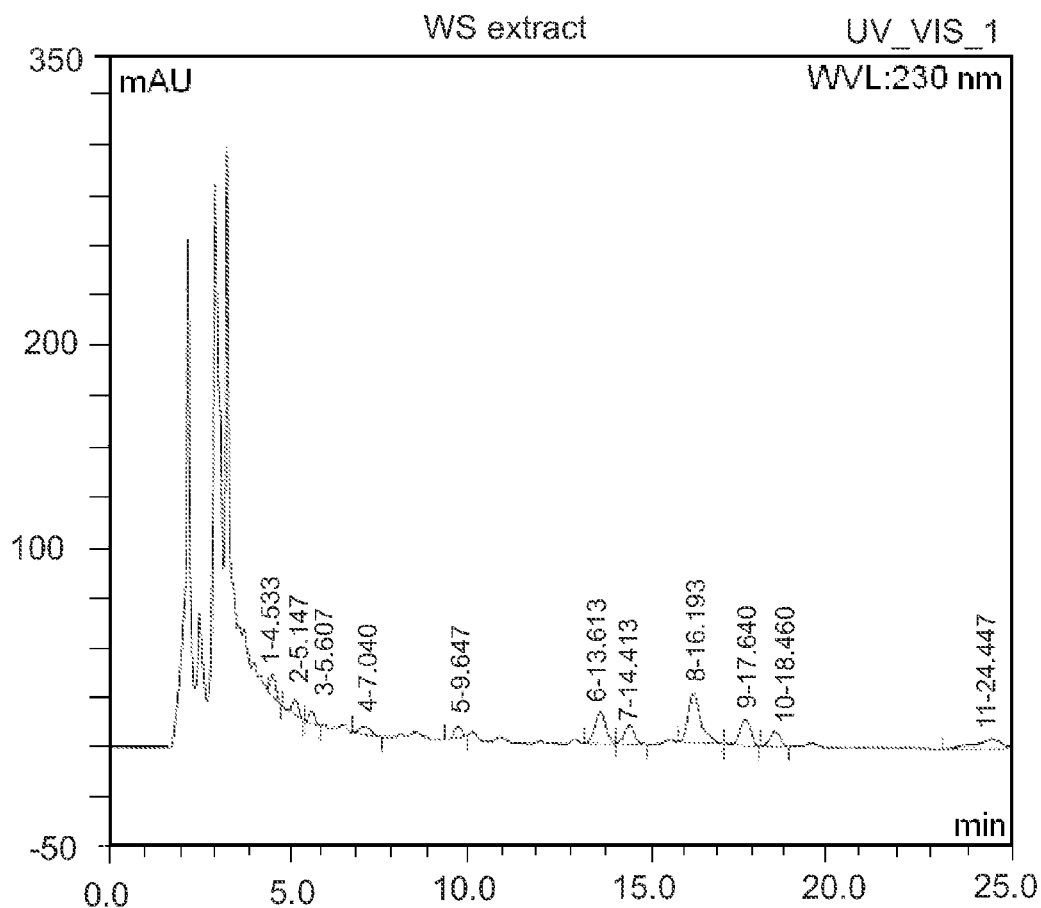
FIG. 6 illustrates chemo-profiling of the extract disclosed in Indian Patent application No. 1253/MUM/2003.

Comparative Chemo-profiling of *Withania somnifera* fraction of the present invention and extract used in Indian patent application No. 1253/MUM/2003 is shown in FIGS. 5 and 6. The content of Withaferin A and Withanolide A in the extract used in Indian patent application No. 1253/MUM/2003 and *Withania somnifera* fraction of the present invention is provided in table 6.

TABLE 6

| Batch | Withaferin A (mg/100 mg) | Withanolide A (mg/100 mg) |
|---|---|---|
| TM-1(1253/MUM/2003) | 0.04585 ± 0.0005 | 0.04785 ± 0.0001 |
| SIIL-F-4(*Withania somnifera* fraction of the present invention) (Scaled up) | 0.853 ± 0.005 | 1.750 ± 0.009 |

Results suggest that the fractionation has resulted in 20 and 40 fold higher enrichment in Withaferin A and Withanolide A respectively.

Example 3

Figure 7:
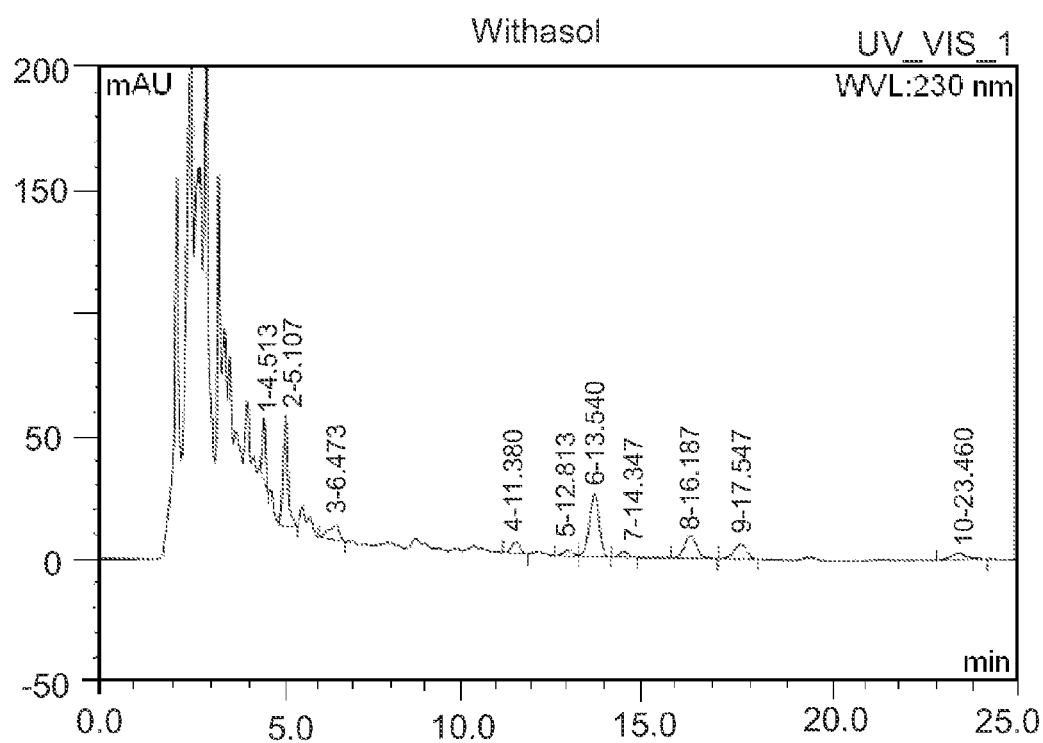
FIG. 7 illustrates chemo-profiling of the fraction disclosed in US20040033273.

Comparative Chemo-profiling of *Withania somnifera* fraction of the present invention (SIIL-F-4) and fraction disclosed in US20040033273 is shown in FIGS. 5 and 7.

The content of Withaferin A and Withanolide A in the fraction used in US20040033273 and *Withania somnifera* Fraction of the present invention is provided in table 7.

TABLE 7

| Batch | Withaferin A (mg/100 mg) | Withanolide A (mg/100 mg) |
|---|---|---|
| US20040033273(Withasol) | Below detection limit | 0.063 ± 0.0006 |
| *Withania somnifera* fraction of the present invention (SIIL-F-4) (Scaled up) | 0.853 ± 0.005 | 1.750 ± 0.009 |

Result indicates that *Withania somnifera* fraction fingerprint is richer in Withaferin A and Withanolide A.

Example 4

Adjuvant Activity of the Adjuvant of the Present Invention when Administered by Oral or Parenteral Route with Meningococal A Vaccine a) Animals: Pathogen-free female swiss albino mice, weighing about 13-18 gm, were randomly distributed in groups as per experimental protocols (n=10). Animals were housed and maintained by following the standard guidance as found in Government of India guidelines (CPCSEA). The study protocol was approved by Institutional Animal Ethics Committee.

b) Meningococcal A polysaccharide vaccine: Meningococcal plain polysaccharide at dose of 5 ug/mouse was used. This polysaccharide was formulated with the adjuvant of the present invention at various doses and was either injected subcutaneously or administered orally to the animals.

c) IgG estimation (Ab-ELISA): The test was carried out using microtiter plate wells (Nunc, maxisorb) with the use of Meningococcal polysaccharide in suitable diluent as a coating solution. Test and reference sera in diluting buffer were added to respective wells. The microtiter plates were maintained for overnight (16 to 18 hrs.) at 2-8° C. in a refrigerator. The plates were washed and secondary antibody (antimouse IgG peroxidase, Amrsham) was added to each well of the plate. After 2 hrs., at room temperature, the plates were washed with wash buffer and freshly prepared substrate solution TMB (Sigma) was added. After 10 min, the colorimetric reaction was stopped by addition of 100 ul of 1 N $H_2SO_4$. Plates were observed at 405/630 nm with the help of microplate Reader (Bio-Tek Instruments Inc.).

d) Study design: Animals were divided into respective groups and were injected subcutaneously above mentioned preparations on day 0, 14 and 28. Sera were collected for IgG estimation on day 14, 28 and 42.

Figure 8:
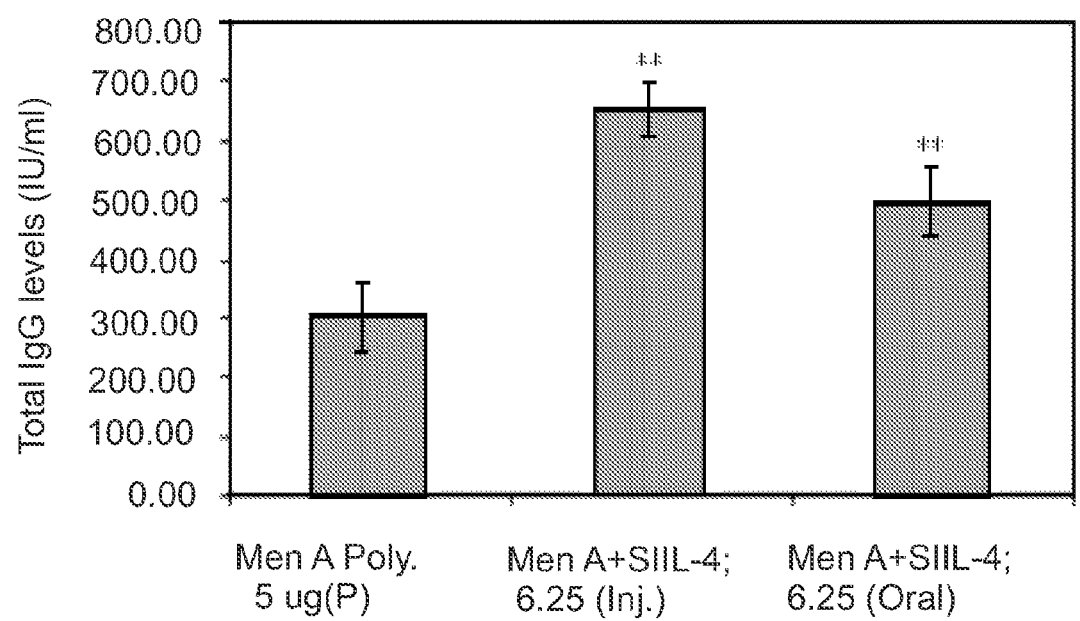
FIG. 8 illustrates adjuvant activity of the adjuvant in accordance with the present invention when administered by oral or parenteral route with Meningococal A vaccine.

Results as shown in FIG. 8 clearly indicate that vaccine containing the adjuvant of the present invention (SIIL-4) was more immunogenic and induced a better IgG response. Further the adjuvant showed adjuvant activity on oral as well as parenteral administration.

Example 5

Adjuvant Activity of the Adjuvant of the Present Invention when Formulated with Vaccine Prior to Injection and the Role of Adsorption in Adjuvant Activity (i.e. when the Adjuvant was Kept Overnight with Vaccine)

a) Animals: Pathogen-free female swiss albino mice, weighing about 13-18 gm., were randomly distributed in groups as per experimental protocols (n=10). Four experiments were carried.

b) Meningococcal A polysaccharide vaccine: Meningococal plain polysaccharide at dose of 5 ug/mouse was used. This polysaccharide was formulated with the said adjuvant at various doses and was either injected subcutaneously or orally to the animals.

c) The vaccine adjuvant of the present invention was mixed with equal volumes of antigen containing solution to form a vaccine in accordance with the present invention which was then shaken vigorously for about 3-4 minutes.
  i) The vaccine was injected into animals immediately.
  ii) The vaccine was kept at 2-8° C. for overnight and was administered to animals next day.
  iii) The vaccine was kept at 2-8° C. for overnight under continuous stirring and was administered to animals next day.

d) IgG estimation (Ab-ELISA): The test was carried out as per example 4.

e) Study design: Animals were divided into respective groups as in example 4

Figure 9:
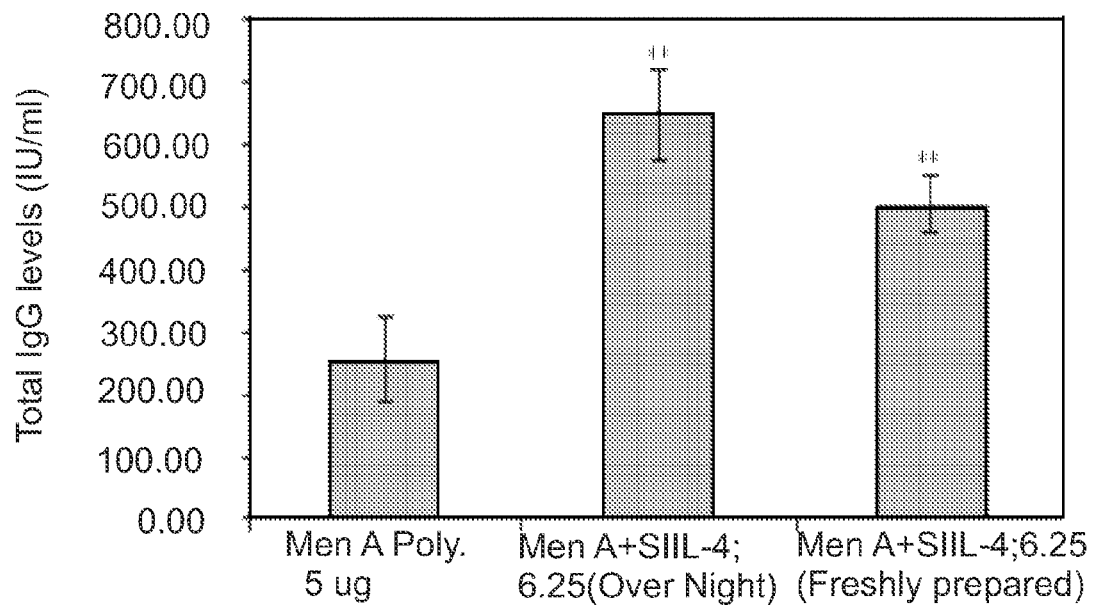
FIG. 9 illustrates adjuvant activity of the adjuvant in accordance with the present invention when formulated with vaccine prior to injection and role of adsorption in adjuvant activity (i.e. when the adjuvant kept overnight with vaccine).

Results as shown in FIG. 9 indicate that the adjuvant of the present invention shows significant adjuvant activity in all the conditions i.e. when used immediately after combining with vaccine and when kept overnight with vaccine. However, the adjuvant of the present invention shows higher adjuvant activity when kept overnight which suggest a possible role of adsorption in its adjuvant activity.

Example 6

Co-Adjuvanicity of Present Adjuvant (SIIL-F-4) with Licensed or Preclinical Adjuvants a) Alum was selected for this study, however the results may be applicable to other adjuvants such as liposomes, MF-59, MPL, CpG, QS-21, etc. This experiment was designed to determine co-adjuvant effect of SIIL-F4 with alum adsorbed DPT vaccine.

DPT vaccine was mixed with adjuvant of the present invention (ADS) and was kept overnight at 2-8° C. Guinea pigs were used as experimental animals. On day 0, animals were immunized with DPT vaccine alone or mixed with ADS. On day 26, a pre-decided number of animals were bleeded for diphtheria antitoxin levels using verocell assay. On day 28, animal were again challenged with diphtheria toxin. Sera were collected on day 33 for antitoxin levels.

b) Estimation of diphtheria antitoxin levels

Following steps were carried out for evaluating anti-diphtheria anti-body titres using vero cells:

1) All serum samples were heat inactivated using water bath at 56° c. for 30 minutes.
2) Required dilutions of standard adjuvant (ADS) solution and toxin were prepared using minimal essential medium (MEM).
3) First well in each row of microtitre plate were labeled with test sample codes.
4) 50 µl of MEM was added in $2^{nd}$ to $9^{th}$ well of each column followed by addition of 50 µl MEM in 2, 3, 4, 5, 6, 7 & $8^{th}$ well of $11^{th}$ to $12^{th}$ column of the microtiter plate (total 100 µl of MEM was added in well no. 7 & 8 of $11^{th}$ to $12^{th}$ column).
5) 100 µl heat inactivated serum samples were added to first wells of first row of the plate, and 50-µl serum samples were further transferred to next consecutive well with proper mixing. This process was carried out till 10th row of the plate, last 50 µl of sample from $10^{th}$ row was discarded. Further, 100 µl ADS was added in first well of $11^{th}$ to $12^{th}$ column of the plate followed by transfer of 50 µl ADS in next well i.e. $2^{nd}$ well of $11^{th}$ & $12^{th}$ column. This process was carried out upto $4^{th}$ well of $11^{th}$ to $12^{th}$ column.
6) Addition of 50 µl toxin in each wells of the plate (except $7^{th}$ & $8^{th}$ well of $11^{th}$ and $12^{th}$ column-cell control) was carried out and plates were kept at room temperature for 1 hr. incubation.
7) After room temperature incubation 100 µl of $4 \times 10^5$ vero cells were added in each wells of the plate, followed by incubation of the plates at 37° c. for 5 days.
8) Toxic effect (+) and healthy cells (−) were observed under inverted microscope and minimum dilution of test sera showing protection was considered as titres. Titres were finally expressed in IU/ml.

Figure 10:
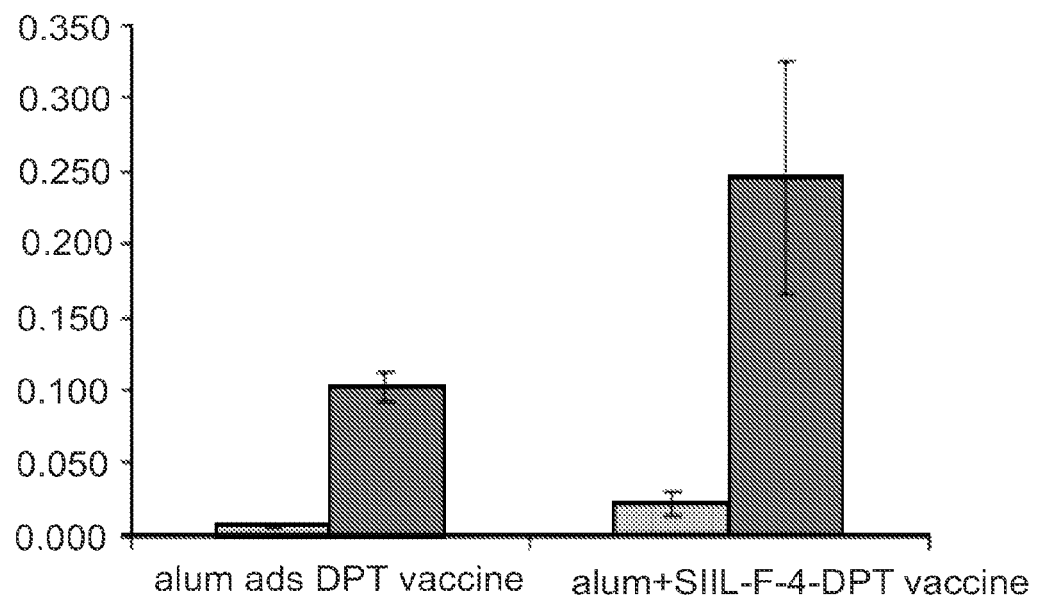
FIG. 10 illustrates co-adjuvanicity of the adjuvant of the present invention (SIIL-F-4) with licensed or preclinical adjuvant.

The results as shown in FIG. 10 suggest that the present adjuvant has a significant co-adjuvant effect with alum, thereby suggesting its possible inclusion in adjuvant containing formulations.

Example 7

Adjuvant Effect of the Adjuvant of the Present Invention (SIIL-F-4) on Th1/Th2 Immunity a) Modulation of Th1/Th2 immunity was carried to optimize immune response against antigens.

b) Immunomodulatory effect on Th1-Th2 balance was determined by estimation of selected cytokine levels produced by Th1 and Th2 cells in vivo using flow cytometry SIIL-F-4 was mixed with polysaccharide antigen. The immunization schedule containing SIIL-F-4 may vary from antigen to antigen basis. The blood samples were collected at suitable intervals and assessed for Th1/Th2 cells or cytokines using flow cytometry. The results are shown in table 8.

TABLE 8

| Groups | Treatment | Th1 cytokines | | Th2 cytokines |
| | | IFN-gamma | IL-2 | IL-4 |
|---|---|---|---|---|
| I | Control (naïve) | 1.24 ± 0.2 | 0.2 ± 0.1 | 0.58 ± 0.1 |
| II | Control (sensitized) | 2.71 ± 0.3 | 6.65 ± 0.4 | 2.9 ± 0.2 |
| III | Alum (NMT, 3.5 mg/ml) | 3.5 ± 0.5 | 9.90 ± 0.4 (P < 0.001)* | 10.91 ± 0.4 (P < 0.001)* |
| IV | SIIL-F-4 (6.25 mg/kg) | 5.4 ± 0.5 (P < 0.001)*, P < 0.001)** | 10.29 ± 0.4 (P < 0.001)*, (P < 0.001)** | 7.02 ± 0.2* (P < 0.001)*, (P < 0.001)** |

These results show significant effects of the adjuvant of the present invention on T-cell immunity which suggest possible reasons for observed increased immunogenicity with T cell independent antigens such as polysaccharide antigens.

Example 8

Comparative Efficacy of the Adjuvant Composition Disclosed in Indian Patent Application No. 1253/MUM/2003 and the Adjuvant of the Present Invention with Meningococcal a Plain Polysaccharide Vaccine a) Animals: Pathogen-free female swiss albino mice, weighing about 13-18 gm., were randomly distributed in groups as per experimental protocols (n=10).
b) Meningococcal A polysaccharide vaccine: Meningocoal plain polysaccharide at dose of 5 ug/mouse was used. This polysaccharide was formulated with the semi-purified fraction of the present invention at various doses and was injected subcutaneously or administered orally to the animals.
c) IgG estimation (Ab-ELISA): The test was carried out as per example 4.
d) Animals were divided into respective groups and were injected subcutaneously above mentioned preparations on day 0, 14 and 28. Sera were collected for IgG estimation on day 42.

Figure 11:
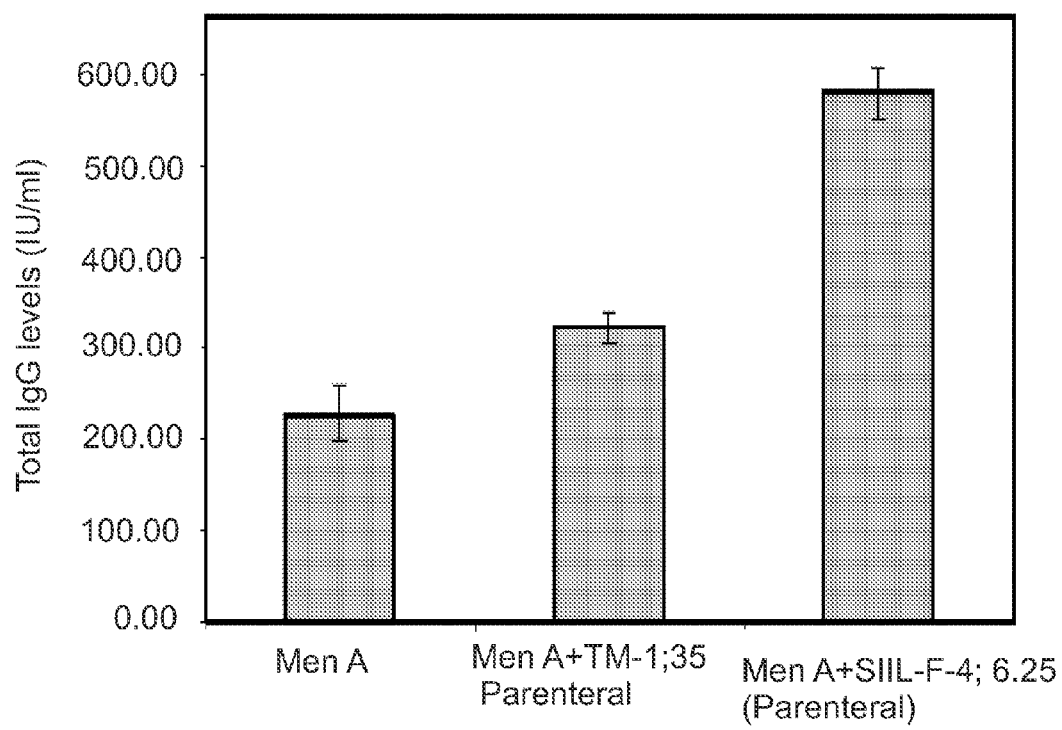
FIG. 11 illustrates comparative efficacy of the adjuvant composition disclosed in Indian patent application No. 1253/MUM/2003 and the adjuvant of the present invention with Meningococcal A plain polysaccharide vaccine.

Results as shown in FIG. 11 suggest that the adjuvant (SIIL-F-4) of the present invention shows higher efficacy as compared to adjuvant composition disclosed in patent application No. 1253/MUM/2003(TM-1).

Example 9

Comparative Adjuvant Activity of the Adjuvant of the Present Invention and the Fraction Disclosed in US20040033273

Figure 12:
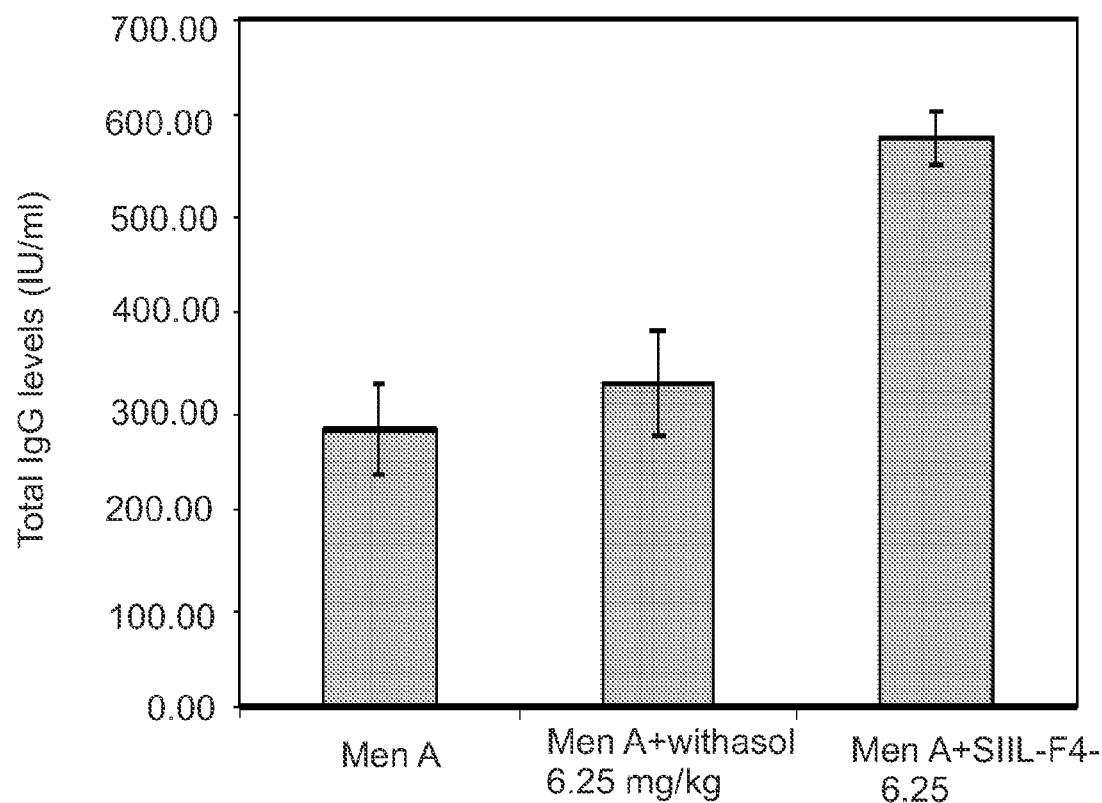
FIG. 12 illustrates comparative adjuvant activity of the present adjuvant and the fraction disclosed in US20040033273.

The study was carried out as per example 8. The results as shown in FIG. 12 suggest that present adjuvant (SIIL-F-4) shows higher adjuvant activity as compared to Withasol fraction disclosed in US20040033273.

Example 10

Comparative Adjuvant Activity of the Present Adjuvant, Methanolic Extract of *Withania somnifera* and Aqueous Extract of *Withania somnifera* on Total Anti-Polysaccharide IgG Levels in Normal Mice The present adjuvant and extracts were administered with Meningococcal A polysaccharide on indicated days and IgG levels were estimated on day 42 to assess adjuvant activity. The results are shown in table 9.

TABLE 9

| Treatment | Dose | Schedule | Total IgG level | Activity (%) |
|---|---|---|---|---|
| Men A (P) | 5 ug/mouse | 14 and 28 day | 287.88 ± 60.28 | NA |
| Men A + present adjuvant (P) | 150 ug/mouse | 14 and 28 day | 579.62 ± 27.24 | 101.41 |
| Men A + methanolic extract of WS (P) | 600 ug/mouse | 14 and 28 day | 375.89 ± 58.64 | 30.62 |
| Men A + aqueous extract of WS (P) | 1200 ug/mouse | 14 and 28 day | 317.28 ± 104.76 | 10.27 |
| Aqueous extract of WS (P) | 900 ug/mouse | 14 and 28 day | 312.34 ± 60.25 | 8.62 |
| Aqueous extract of WS (P) | 900 ug/mouse | 7, 14, 21 and 28 day | 410.73 ± 15.91 | 42.40 |
| Aqueous extract of WS (O) | 2400 ug/mouse | Once daily for 14 days (day 0-14) | 437.57 ± 39.87 | 52.32 |
| Withaferin A(P) | 0.011 mg/kg | 14 and 28 day | 397.47 ± 93.71 | 38.12 |
| Withanolide A(P) | 0.0185 mg/kg | 14 and 28 day | 329.84 ± 86.82 | 14.62 |
| Both markers (P) | Mixture as on above doses | 14 and 28 day | 479.76 ± 90.24 | 66.74 |

P = Parenteral administration,
O = Oral administration,
WS = *Withania somnifera*.
All values are shown as Mean ± SE. Percent immunomodulatory activity was calculated using formulae: Immunomodulatory activity (test group-control)/control group *100.
NA = Not applicable.
N = 10

The results show that:
i) when the methanolic extract of *Withania somnifera* is administered parenterally (2 times application, 600 μg/mouse) it result in adjuvant activity (percent enhancement) of 30.62%
ii) when the aqueous extract of *Withania somnifera* is administered parenterally (5 times application, 900 μg/mouse) it result in adjuvant activity (percent enhancement) of 52.32%
iii) when present adjuvant (containing specific ratios of Withanolide A and Withaferin A) is administered parenterally (2 times application, 150 μg/mouse) it result in adjuvant activity (percent enhancement) of 101.41%

The results indicate that the adjuvant of the present invention shows much higher adjuvant activity compared to known adjuvant composition. Further, the amount and frequency of the present adjuvant required to produce higher adjuvant activity are reduced compared to known adjuvant compositions.

While considerable emphasis has been placed herein on the specific features of the preferred embodiment, it will be appreciated that many additional features can be added and that many changes can be made in the preferred embodiment without departing from the principles of the invention. These and other changes in the preferred embodiment of the invention will be apparent to those skilled in the art from the disclosure herein, whereby it is to be distinctly understood that the foregoing descriptive matter is to be interpreted merely as illustrative of the invention and not as a limitation.

The invention claimed is:
1. A method for preparing a *Withania somnifera* fraction rich in withanolides; said method comprising the steps of:
 a) obtaining coarse root material of the *Withania somnifera* plant and refluxing with boiling water to obtain a slurry;
 b) filtering and vacuum concentrating the slurry to obtain a concentrated aqueous extract;
 c) liquid-liquid successive partitioning of the concentrated aqueous extract with at least one non-polar organic solvent and at least one polar organic solvent comprising butanol to obtain an organic fraction of the extract; and
 d) concentrating and co-distilling the organic fraction under vacuum to remove traces of solvent followed by drying the fraction at a temperature of not more than 70° C. to obtain a *Withania somnifera* fraction rich in withanolides.

2. The method of claim 1, wherein the non polar organic solvent is selected from the group consisting of n-hexane, toluene and benzene.

3. A *Withania somnifera* fraction rich in withanolides; said fraction comprising a) withanolide A of about 0.5-1%; b) withaferin A of about 0.1-0.6%; c) withanolide B of about 0.01-0.1%; d) withanoside IV of about 0.8-1.2%; e) withanoside V of about 0.5-0.8%; and f) 12-deoxy withastramonolide of about 0.8-1.2%; wherein the ratio of withaferin A to withanolide A is in the range of about 1:2 to about 1:5.

4. A vaccine prepared in accordance with the method recited in claim 1, the vaccine comprising:
 a. an antigen comprising serogroup A meningococcal polysaccharide, and
 b. an adjuvant comprising "*Withania somnifera* fraction", said fraction comprising withanolide A and withaferin A, in an amount of about 85 to 99% of the mass of the vaccine.

5. The vaccine of claim 4, wherein the proportion of withanolide A is in the range of about 0.1 to about 5% of the mass of the fraction.

6. The vaccine of claim 4, wherein the proportion of withaferin A is in the range of about 0.1 to about 3% of the mass of the fraction.

7. The vaccine of claim 4, further comprising alum-hydroxide as a co-adjuvant.

8. The vaccine of claim 4, wherein the concentration of the adjuvant is about 150 µg/single dose.

9. The vaccine of claim 1, wherein the polar organic solvent is limited to only butanol.

\* \* \* \* \*